US006416778B1

(12) United States Patent
Ragavan et al.

(10) Patent No.: US 6,416,778 B1
(45) Date of Patent: Jul. 9, 2002

(54) PHARMACEUTICAL PREPARATIONS AND METHODS FOR THEIR REGIONAL ADMINISTRATION

(75) Inventors: Vanaja V. Ragavan, Wynnewood; Gerianne M. DiPiano, Malvern, both of PA (US)

(73) Assignee: FemmePharma, Wayne, PA (US)

( * ) Notice: Subject to any disclaimer, the term of this patent is extended or adjusted under 35 U.S.C. 154(b) by 0 days.

(21) Appl. No.: 09/355,213

(22) PCT Filed: Jan. 23, 1998

(86) PCT No.: PCT/US98/00916

§ 371 (c)(1),
(2), (4) Date: Jul. 23, 1999

(87) PCT Pub. No.: WO98/32422

PCT Pub. Date: Jul. 30, 1998

Related U.S. Application Data

(60) Provisional application No. 60/036,727, filed on Jan. 24, 1997, and provisional application No. 60/052,578, filed on Jul. 15, 1997.

(51) Int. Cl.[7] ............................................. A61K 9/14

(52) U.S. Cl. ...................... 424/430; 424/433; 424/489; 514/899; 514/937; 514/944; 514/945; 514/967; 514/969

(58) Field of Search ........................... 424/430, 464, 424/433, 489

(56) References Cited

U.S. PATENT DOCUMENTS

| | | |
|---|---|---|
| 3,921,636 A | 11/1975 | Zaffaroni |
| 3,927,216 A * | 12/1975 | Witkowski et al. ......... 424/269 |
| 4,081,533 A | 3/1978 | Cheesman |
| 4,107,288 A | 8/1978 | Oppenheim et al. |
| 4,272,398 A | 6/1981 | Jaffe |
| 4,286,587 A | 9/1981 | Wong |
| 4,291,028 A | 9/1981 | Vorys |
| 4,292,315 A | 9/1981 | Vorys |
| 4,391,797 A | 7/1983 | Folkman et al. |
| 4,525,340 A | 6/1985 | Lange et al. |
| 4,591,496 A | 5/1986 | Cohen et al. |
| 4,673,405 A | 6/1987 | Guittard et al. |
| 4,762,717 A | 8/1988 | Crowley, Jr. |
| 4,861,627 A | 8/1989 | Mathiowitz et al. |
| 4,873,092 A | 10/1989 | Azuma et al. |
| 4,919,939 A | 4/1990 | Baker |
| 4,965,128 A | 10/1990 | Greidanus et al. |
| 4,997,653 A | 3/1991 | Igarashi |
| 5,057,317 A | 10/1991 | Iida |
| 5,091,185 A | 2/1992 | Castillo et al. |
| 5,130,137 A | 7/1992 | Crowley, Jr. |
| 5,145,684 A * | 9/1992 | Liversidge et al. ......... 424/489 |
| 5,156,851 A | 10/1992 | Castillo et al. |
| 5,324,522 A | 6/1994 | Krenning et al. |
| 5,330,768 A | 7/1994 | Park et al. |
| 5,340,585 A | 8/1994 | Pike et al. |
| 5,359,030 A | 10/1994 | Ekwuribe |
| 5,362,720 A | 11/1994 | Labrie |
| 5,413,797 A | 5/1995 | Khan et al. |
| 5,417,982 A | 5/1995 | Modi |
| 5,434,146 A | 7/1995 | Labrie |
| 5,438,040 A | 8/1995 | Ekwuribe |
| 5,472,704 A | 12/1995 | Santus et al. |
| 5,482,925 A | 1/1996 | Hutsell |
| 5,482,927 A | 1/1996 | Maniar et al. |
| 5,494,047 A | 2/1996 | Van Os |
| 5,510,118 A | 4/1996 | Bosch et al. |
| 5,633,011 A | 5/1997 | Dong et al. |
| 5,643,604 A | 7/1997 | Uribe et al. |
| 5,651,976 A | 7/1997 | Price et al. |

FOREIGN PATENT DOCUMENTS

| | | |
|---|---|---|
| EP | 0 501 056 A1 | 9/1992 |
| EP | 0 566 135 A1 | 10/1993 |
| WO | WO95/07071 A1 | 3/1995 |
| WO | WO96/37232 A1 | 11/1996 |

OTHER PUBLICATIONS

Physicians Desk Reference, Terazol 7, Rice et al, 1996, 50 th Edition, p. 1887–1888.*
Physicans Desk Reference, Sultrin, Rice et al, 1996, 50 th Edition, p. 1885–1886.*
Benita, et al., "Characterization of Drug–Loaded Poly(d, l–lactide) Microspheres," *J. Pharm. Sci.* 73(12):1721–1724 (1984).
Braun, et al., "Effect of danazol in vitro and in vivo on monocyte–mediated enhancement of endometrial cell proliferation in women with endometriosis," *Fertility and Sterility* 62(1):89–95 (1994).
De Ziegler, et al., "Administration Non–Orale De La Progestérone: Expériences et Avenir De La Voie Transvaginale,"*Rev. Med. Suisse Romande*, pp. 13–28 (1994).
Farquhar, "Management of Dysfunctional Uterine Bleeding," *Drugs* 44(4):378–384 (1992).
Goodman & Gilman, *The Pharmacological Basis of Therapeutics*, (9th Ed., McGraw–Hill Publishing company (1996).
Hull & Stelling, "Endometriosis: An Enigmatic Disease," *Journal of Women's Health* 5(2):111–120 (1996).

(List continued on next page.)

*Primary Examiner*—James M. Spear
(74) *Attorney, Agent, or Firm*—Patrea L. Pabst; Holland & Knight LLP

(57) ABSTRACT

Formulations have been developed for regional delivery of drugs, for example, into a cavity such as the pelvic region, peritoneal region, or directly on organs of interest. Regional delivery increases comfort and bioavailability of the drug, resulting in rapid and relatively high blood levels in the regions to be treated in the substantial absence of side effects due to the high levels required for efficacy following systemic delivery. In the preferred embodiment, these formulations consist of drug micro or nanoparticles, which may be formed of drug alone or in combination with an excipient or polymeric carrier. The excipient or polymer may be used to manipulate release rates and to increase adhesion to the affected region. The drug formulation can be applied as a dried powder, a liquid suspension or dispersion, or as a topical ointment, creme, lotion, foam or suppository.

26 Claims, No Drawings

OTHER PUBLICATIONS

Igarashi, "A New Therapy for Pelvic Endometriosis and Uterine Adenomyosis: Local Effect of Vaginal and Intrauterine Danazol Application," *Asia–Oceania J. Obstet. Gynaecol.* 16(1):1–12 (1990).

Lim & Moss, "Microencapsulation of Living Cells and Tissues," *J. Pharm. Sci.* 70(4):351–354 (1981).

Lobo, "Vaginal Route Paradox: A Direct Transport to the Uterus," *Symposium: The First Uterine Pass Effect*, (Wyeth–Ayerst International, Inc., 1995).

Martindale, *The Extra Pharmacopoeia*, 31st Ed., *The Pharmaceutical Press*, London (1996).

Mathiowitz, et al., "Morphology of Polyanhydride Microsphere Delivery System," *Scanning Microscopy* 4(2):329–340 (1990).

Mathiowitz, et al., "Novel Microcapsules for Delivery Systems," *Reactive Polymers* 6:275–283 (1987).

Mathiowitz, et al., "Polyanhydride Microspheres as Drug Carriers I. Hot–Melt Microencapsulation," *J. Controlled Release* 5:13–22 (1987).

Mathiowitz, et al., "Polyanhydride Microspheres as Drug Carriers. II. Microencapsulation by Solvent Removal," *J. Appl. Polymer Sci.* 35:755–774 (1988).

Mathiowitz, et al., "Polyanhydride Microspheres. IV. Morphology and Characterization of Systems Made by Spray Drying," *J. Appl. Polymer Sci.* 45:125–134 (1992).

Mizutani, et al., "Danazol concentrations in ovary, uterus, and serum and their effect on the hypothalamic–pituitary–ovarian axis during vaginal adminstration of a danazol suppository," *Fertility and Sterility* 63(6):1184–1189 (1995).

Salib, et al., "Utilization of Sodium Alginate in Drug Microencapsulation," *Pharmazeutische Industrie* 40–11A:1230–1234 (1978).

Spooner, *Classification of Side Effects to Danazol Therapy*, Winthrop Laboratories, Surrey, England.

"The First Uterine Pass Effect—A new finding for new options in progesterone therapy," (West –Ayerst International, Inc., 1995).

Igarashi, "A new therapy for pelvic endometriosis and uterine adenomyosis: Local effect of vaginal and intrauterine danazol application," *Asia–Oceana J. Obstet Gynaecol* 15(1):1–12 (1990).

Physicians' Desk Reference, Consult 1994 Supplements for Revisions, pp. 1372–1375.

* cited by examiner

PHARMACEUTICAL PREPARATIONS AND METHODS FOR THEIR REGIONAL ADMINISTRATION

This application is a 371 of PCT/US 98/00916 filed Jan. 23, 1998 and claims benefit of Provisional Application Nos. 60/036,727 - Jan. 24, 1997, 60/052,578 - Jul. 15, 1997.

FIELD OF THE INVENTION

The present invention relates to pharmaceutical preparations, and especially pharmaceutical formulations that can be introduced topically, locally, intrapelvically, intraperitoneally or directly on reproductive organs of interest in amounts effective to treat various conditions, particularly local diseases of the female reproductive system, such as pelvic, uterine, cervical and vaginal diseases which are present in this region of the body.

BACKGROUND OF THE INVENTION

It has long been known that treatment of female reproductive diseases by traditional methods of oral or systemic administration is associated with drug bioavailability problems and concomitant side effect complications from unwanted absorption of drugs into the systemic circulation. For example, normal digestive tract action may break down orally administered active ingredients to decrease effective drug delivery dosages, or the pharmaceutical preparation may be changed by passage through the liver or by systemic circulation or may not achieve adequate levels in the area of interest. To counteract these undesirable actions, the dosage of the active ingredient needs to be increased, oftentimes leading to undesirable side effects.

Danazol, an isoxazolo derivative of 17 ethenyltestosterone (an androgen hormone), is commonly administered to women for treatment of endometriosis, range up to 800 mg daily. At high doses, adverse side effects are seen which may include weight gain, voice change, development of facial and chest hair, loss of libido, acne, and central nervous system ("CNS") symptoms such as depression, anxiety, fatigue, nausea and diarrhea, as well as the inhibition of pregnancy while undergoing treatment. See, for example, Spooner, *Classification of Side Effects to Danazol Therapy*, Winthrop Laboratories, Surrey, England.

It is therefore highly desirable to provide new systems and methods for the administration of pharmaceuticals which would avoid such drawbacks. Mizutani, et al., in *Fertility and Sterility* 63, 1184–1189 (1995), describes administration of danazole vaginally by means of a 100 mg suppository, and compared the results with oral administration of a 400 mg dosage. No effect on the hypothalamic-pituitary-ovarian axis was noted, although high concentrations were present in the ovary, uterus and serum, with insignificant serum levels, following vaginal administration. Mizutani, et al., conducted their study following a report by Igarishi, *Asia-Oceania J. Obstet. Gynaecol.* 16(1), 1–12 (1990), that administration of danazole in a silicone vaginal ring reduced endometriotic tissue in the uterus and increased the incidence of pregnancy in treated women to a statistically significant degree. The immediate drawback to both therapies, however, is that the formulation and delivery platform such as vaginal rings and other devices are particularly unsatisfactory for women who already suffer from the cramps and pains associated with endometriosis. The dosages which were used were also quite high and extremely variable and may potentially have a negative and accumulative depot effect.

Igarashi's implant, and other proposed danazole formulations for local release of danazol for treatment of endometriosis, wherein the effect is achieved by direct administration of the danazole to the tissue to be treated, are described in U.S. Pat. No. 4,997,653 to Igarashi and EPA 0 501 056 (col. 2, lines 24–29 of the U.S. patent).

Many other drug delivery systems are available, but have not been developed for this purpose. Examples include U.S. Pat. No. 3,921,636 to Zaffaroni, which describes a drug delivery reservoir for controlled, sustained release of water soluble materials as a function of diffusion of water into the device and dissolution of the drug to be released for systemic or local effect (col. 10, line 46). EPA 0 566 135 by Takeda Chemical Industries describes a preparation for systemic delivery of proteins or peptides via the mucosal regions such as the mouth or vagina, wherein delivery is enhanced by inclusion of a cytidine nucleotide derivative. WO 96 37232 by Universidade de Santiago de Compostela describes complexes of nanoparticules, emulsions or nanocapsules within a matrix formed by ionic complexing of a water soluble positively charged amino polysaccharide and a negatively charged phospholipid, which are useful for topical or transmucosal administration of drugs. WO 95 07071 by Edko Trading describes an ointment or creme for intravaginal administration of antifungal drugs. U.S. Pat. No. 5,510,118 to Nanosystems describes preparation of a powder consisting solely of nanoparticles of drugs, such as danazole, which is highly soluble and therefore advantageous for systemic administration by injection.

It is therefore an object of the present invention to provide formulations which are effective in treating disorders of the reproductive system.

It is therefore an object of the present invention to provide formulations which are effective in treating disorders of the reproductive organs which has high patient compliance and comfort.

It is a further object of the present invention to provide formulations and methods of administration which provide for extremely rapid uptake of drug in the affected region, with low systemic concentrations and few concordant side effects.

It is still another object of the present invention to provide greatly enhanced bioavailability of drug in formulations administered topically or locally, intrapelvically, intraperitoneally or directly on reproductive organs of interest as compared to the drugs administered in controlled release devices.

SUMMARY OF THE INVENTION

Formulations have been developed for topical or local delivery of drugs intrapelvically, intraperitoneally or directly onto organs of interest, to produce a regional effect, with lower systemic drug levels than obtained when an effective dosage is systemically administered. In a preferred embodiment, drug is administered to a region such as the female reproductive system, provide for increased comfort, increased bioavailability, rapid and relatively high blood levels in the region to be treated without causing systemic levels of drug which might cause side effects. The preferred formulations consist of drug micro or nanoparticles, which may be formed of drug alone or in combination with an excipient or polymeric carrier. The excipient or polymer may be used to manipulate release rates and to increase adhesion of the drug to the affected region. The drug formulation can be applied as a dry powder, a liquid suspension or dispersion, a hydrogel suspension or dispersion, sponges, or as a topical ointment, creme, lotion, foam or suppository.

Specific danazole formulations are described. Rat studies demonstrate rapid uptake of danazole into the tissues affected in endometriosis, with serum drug levels that are almost undetectable.

DETAILED DESCRIPTION OF THE INVENTION

The compositions and methods for administration thereof provide for significantly diminished side effects with increased bioavailability and comfort, as compared to conventional drug administration techniques, and avoid the need for oral and parenteral administration, the use of complex and expensive biocompatible polymeric material, and insertion into the body and maintenance therein of potentially infectious foreign objects, such as intrauterine devices, vaginal rings, and suppositories.

I. Formulations

The formulations are designed to provide maximum uptake in the affected tissues with rapid dissemination throughout the region to be treated, with little to no increase in systemic blood levels of the drug. The formulations can consist solely of drug, or drug combined with excipient or polymeric material.

A. Drugs

The term "drug" can refer to any pharmaceutically active substance capable of being administered in a particulate formulation, which achieves the desired effect. Drugs can be synthetic or natural organic compounds, proteins or peptides, oligonucleotides or nucleotides, or polysaccharides or sugars. Drugs may have any of a variety of activities, which may be inhibitory or stimulatory, such as antibiotic activity, antiviral activity, antifungal activity, steroidal activity, cytotoxic or anti-proliferative activity, anti-inflammatory activity, analgesic or anesthetic activity, or be useful as contrast or other diagnostic agents. A description of classes of drugs and species within each class can be found in Martindale, *The Extra Pharmacopoeia*, 31st Ed., *The Pharmaceutical Press*, London (1996) and Goodman and Gilman, *The Pharmacological Basis of Therapeutics*, (9th Ed., McGraw-Hill Publishing company (1996).

Examples of compounds with steroidal activity include progestins, estrogens, antiestrogens and antiprogestins.

In a preferred embodiment, the drug is danazole or gestrinone in a micro or nanoparticulate formulation. This can be achieved by milling of the drug or atomization of drug solution, for example, into a solvent extraction fluid, or other standard techniques. The danazole or gestrinone can be present as a complex with a cyclodextrin, for example, hydroxypropyl-β-cyclodextrin (HPB).

In another preferred embodiment, the drug is a polysaccharide, preferably a sulfated polysaccharide. Examples of suitable sulfated polysaccharides include carageenan, dextran sulfate, heparin, and fucoidin.

B. Excipients or Carriers

The drug substance may be "associated" in any physical form with a particulate material, for example, adsorbed or absorbed, adhered to or dispersed or suspended in such matter, which may take the form of discrete particles or microparticles in any medicinal preparation, and/or suspended or dissolved in a carrier such as an ointment, gel, paste, lotion, sponge, or spray.

Standard excipients include gelatin, casein, lecithin, gum acacia, cholesterol, tragacanth, stearic acid, benzalkonium chloride, calcium stearate, glyceryl monostearate, ceto- stearyl alcohol, cetomacrogol emulsifying wax, sorbitan esters, polyoxyethylene alkyl ethers, polyoxyethylene castor oil derivatives, poly-oxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches.

C. Polymeric Materials

In a preferred embodiment, the drug is present on or within micro or nanoparticulates formed of a polymeric material. Additional materials, such as diagnostic agents, including echogenic gases, radioactive materials - which may also in themselves be therapeutic, and magnetic materials for detection by MRI or PET, can optionally be included in the particles.

Various polymers can be used to increase adhesion to mucosal surfaces, to control release as a function of the diffusion rate of drugs out of the polymeric matrix and/or rate of degradation by hydrolysis or enzymatic degradation of the polymers and/or pH alteration, and to increase surface area of the drug relative to the size of the particle.

The polymers can be natural or synthetic, and can be biodegradable or non-biodegradable. High molecular weight drugs can be delivered partially by diffusion but mainly by degradation of the polymeric system. For this reason, biodegradable polymers, bioerodible hydrogels, and protein delivery systems are particularly preferred when high molecular weight drugs are being delivered.

The polymers may be natural or synthetic polymers, although synthetic polymers are preferred due to the better characterization of degradation and release profiles. The polymer is selected based on the period over which release is desired, generally in the range of at least immediate release to release over a period of twelve months, although longer periods may be desirable. In some cases linear release may be most useful, although in others a pulse release or "bulk release" may provide more effective results. The polymer may be in the form of a hydrogel (typically absorbing up to about 90% by weight of water), and can optionally be crosslinked with multivalent ions or polymers.

Representative natural polymers include proteins such as zein, modified zein, casein, gelatin, gluten, serum albumin, and collagen, polysaccharides such as cellulose, dextrans, and polyhyaluronic acid.

Representative synthetic polymers include polyphosphazenes, poly(vinyl alcohols), polyamides, polycarbonates, polyacrylates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof.

Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

Synthetically modified natural polymers include cellulose derivatives such as alkyl celluloses, hydroxyalkyl celluloses, cellulose ethers, cellulose esters, and nitrocelluloses.

Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

Each of the polymers described above can be obtained from commercial sources such as Sigma Chemical Co., St. Louis, Mo., Polysciences, Warrenton, Pa., Aldrich Chemical Co., Milwaukee, Wis., Fluka, Ronkonkoma, N.Y., and BioRad, Richmond, Calif. or can be synthesized from monomers obtained from these suppliers using standard techniques. The polymers described above can be separately characterized as biodegradable, non-biodegradable, and bioadhesive polymers, as discussed in more detail below.

1. Biodegradable Polymers Representative synthetic degradable polymers include polyhydroxy acids such as polylactides, polyglycolides and copolymers thereof, poly (ethylene terephthalate), poly(butic acid), poly(valeric acid), poly(lactide-co-caprolactone), polyanhydrides, polyorthoesters and blends and copolymers thereof.

Representative natural biodegradable polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers. In general, these materials degrade either by enzymatic hydrolysis or exposure to water in vivo, by surface or bulk erosion.

2. Non-Biodegradable Polymers

Examples of non-biodegradable polymers include ethylene vinyl acetate, poly(meth)acrylic acid, polyamides, polyethylene, polypropylene, polystyrene, polyvinyl chloride, polyvinylphenol, and copolymers and mixtures thereof.

3. Bioadhesive Polymers

Hydrophilic polymers and hydrogels tend to have bioadhesive properties. Hydrophilic polymers that contain carboxylic groups (e.g., poly[acrylic acid]) tend to exhibit the best bioadhesive properties. Polymers with the highest concentrations of carboxylic groups are preferred when bioadhesiveness on soft tissues is desired. Various cellulose derivatives, such as sodium alginate, carboxymethylcellulose, hydroxymethylcellulose and methylcellulose also have bioadhesive properties. Some of these bioadhesive materials are water-soluble, while others are hydrogels.

Rapidly bioerodible polymers such as poly(lactide-co-glycolide), polyanhydrides, and polyorthoesters, whose carboxylic groups are exposed on the external surface as their smooth surface erodes, can also be used for bioadhesive drug delivery systems. In addition, polymers containing labile bonds, such as polyanhydrides and polyesters, are well known for their hydrolytic reactivity. Their hydrolytic degradation rates can generally be altered by simple changes in the polymer backbone. Upon degradation, these materials also expose carboxylic groups on their external surface, and accordingly, these can also be used for bioadhesive drug delivery systems.

D. Hydrogel Matrices

In another preferred embodiment, the drug is present as a dispersion of micro- or nanoparticles in a hydrogel matrix. The hydrogel matrix can be used to cause the particles to remain at a particular location over an extended period of time, particularly when the hydrogel is adhered to a tissue surface. The use of hydrogels to provide local delivery of drugs is described, for example, in U.S. Pat. No. 5,410,016 to Hubbell et al.

The particles to be incorporated in the hydrogel matrix can be formed of drug alone, or can include the excipients and/or polymers described above. The drug can also be added as a dispersion or solution to the matrix. The drug can be released from the particles through dissolution of the particles, the hydrogel or both. Suitable hydrogels can be formed from synthetic polymers such as polyethylene glycol, polyethylene oxide, polyvinyl alcohol, polyvinyl pyrrolidone, polyacrylates, poly (ethylene terephthalate), poly(vinyl acetate), and copolymers and blends thereof, as well as natural polymers such as cellulose and alginate, as described above. Exemplary materials include SEPTRA-FILM™ (modified sodium hyaluronate/carboxymethylcellulose, Genzyme Pharmaceuticals) and INTERCEED™ (oxidized regenerated cellulose, Johnson & Johnson Medical, Inc.)

II. Methods of Administration

The formulations are preferably administered locally within the region to be treated, for example, vaginally for treatment of diseases of the ovaries and uterus. As used herein, "locally" can refer to topical application generally to the mucosal or endometrial surfaces of the vagina and/or uterus, or to a particular portion of the vagina or uterus. As used herein, "regionally" refers to reproductive organs and their surrounding environs, which include uterus, fallopian tube, peritoneal space, pelvic cul-de-sac, ovaries, perineum, abdominal; the rectovaginal region and corresponding regions in men, and urinogenital tract, including bladder, urinary tract, and rectum. As used herein, "systemically" refers to the circulatory system, and regions outside the spaces described above.

Vaginally administered pharmaceutical preparations as described herein are particularly effective in treating certain diseases of female reproductive systems, such as the administration of danazol for treatment of endometriosis, and in the treatment of other disorders such as urinary incontinence. It is desirable to administer the danazol formulations locally with dosages which are less than other modes of delivery, such as oral delivery. Transdermal doses are usually found to be one-quarter of the oral dose for similar efficacy. In this instance, it is possible to lower the dose even lower (the ring delivered between about 1 and 2 mg/day). Such dosage administration will ensure negligible or relatively low serum levels of danazol to avoid undesirable side effects associated with oral dosing, such as hirsutism and other androgenic side effects.

The following non-limiting examples more fully demonstrate the present invention.

EXAMPLE 1

Preparation of Gel Products

The drug substance, micronized danazol (carrying DMF-Drug Master File Certification) was manufactured by Cipla Pharmaceuticals and bought from Byron Chemical Company. UV absorption identified the drug substance as being identical to Danazol USP. Individual impurities were noted to be not more than 0.5%, and total impurities not more than 1.0%. Assay of dried basis was between 97% and 102% w/w on dried basis. More than 90% of the particles were less than 5 microns in diameter and the remaining particles were between 5 and 15 microns in diameter.

Micronized danazol was levigated in a commercial preparation of KY Jelly, which is made up of a polymer hydroxyethyl cellulose to 10 ml volume (based on weight using density of jelly of 2.16 g/ml) to deliver a dosage of 1 mg in 50 μl. Gels were smooth in consistency, uniformly white and flowable. Particle size measurements were conducted with a Coulter H4mD particle size analyzer and were noted to be as follows:

Danazol Powder:

| Average of 6 measurements | 3.2 μg |
|---|---|
| Individual measurement and variation | 3.2 μg ± 9 μg |

1 mg gel:

| Average of 5 measurements | 3.0 μg |
|---|---|
| Individual measurement and variation | 3.4 μg ± 1.5 μg |

EXAMPLE 2

Administration of Danazole Microparticulate Formulation to Rats

Mature female Sprague-Dawley rats were used for the experiment. 1 mg of the microparticulate danazol was delivered in a volume of 50 μl to the vaginal vault and the animals sacrificed at the times noted below. The uterus and ovaries were separately homogenized and blood was drawn. All tissues and biological samples were processed. Danazol was extracted and assayed by HPLC methodology.

Danazol Clinical Assay

Danazol was extracted from serum and tissue hexane/chloroform 80/20. For tissues, 1 ml aliquote of each homogenate was taken. The extracted danazol was reconstituted in a water/acetonitrile mobile phase and a Beckman Ultrasphere 5 micron, 4.6 mm×15 cm reverse phase column (C-18 RP) was used for all the HPLC analyses. A danazol recovery study was conducted using danazol drug product. The recovery was determined by comparing the extracted signal with unextracted signal. A recovery of between 75 and 84% was obtained for the extraction method.

Study Results:

Tissue and serum levels are summarized below in Table 1:

TABLE 1

| Tissue and Serum Levels of Danazole in Rats | | | |
|---|---|---|---|
| RATE AND TIME | UTERUS-ng/g | OVARIES ng/g | SERUM ng/ml |
| 2 hours | 0.43 | 0.33 | 0.21 |
| 4 hours | 0.57 | not detected | not detected |
| 6 hours | 0.77 | not detected | not detected |

The results of this study demonstrate that the formulation used resulted in a preferential absorption of danazol into the uterus.

In the above examples, danazol concentrations of 1 mg/300 g rat were administered. In work by Mizutami, danazol concentrations of 100 mg/50 kg women were administered. These concentrations are roughly equivalent. The data demonstrate that the suppository used by Mizutami resulted in uterine concentrations of danazol which were $10^5$ times higher than the uterine concentrations of danazol provided by the microparticles in the above examples. Such high local concentrations could result in significant changes in the local delivery of the drug and effects on the reproductive organs, for instance, changes in hormone steroid responsiveness and depot effect.

Igarashi administered a vaginal ring contained in silicone. This type of drug delivery device releases drug in a constant manner, creating a continuous flow of drug and potentially to a depot effect. Igarashi discloses two examples in which danazol was administered via the vaginal ring. In both examples, the uterine concentration of danazol was 100 times higher than the uterine concentration in the above examples.

EXAMPLE 3

Protocol for Studies in Primate Models of Endometriosis

Microparticle formulation allows for considerable decrease in delivered dose, increased bioavailability to the organs of interest with lower tissue concentrations.

Monkey Protocol

The monkey study will demonstrate efficacy of the microparticle formulation in an animal model of endometriosis, while also evaluating systemic levels of locally delivered danazol. The simian model of endometriosis will be used to demonstrate efficacy and safety. The rationale for using monkeys is the finding that certain monkeys will naturally develop endometriosis which resembles, in crucial ways, the human disease. In addition, monkeys are a good model for studying the human female reproductive system, both anatomically and physiologically for testing a vaginal product such as Danazol TVDT. This study will assist in identifying the dose needed to treat human endometriosis and furthermore, corroborate preliminary evidence that danazol can be delivered vaginally for treatment of endometriosis with reduced systemic levels. Microparticle danazol will be formulated in the presence of poly(vinylpyrrolidone). Three doses of Danazol TVDT will be studied in monkeys with endometriosis and compared to orally delivered danazol as described below. The study will be a nine week, parallel, randomized study comparing the effects of oral danazol given at 200 mg daily and three doses of Danazol TVDT: at 10 mg/day; (one-twentieth the oral dose), 25 mg/day (one-tenth the oral dose) and 50 mg/ day, (one quarter the oral dose). The results will demonstrate local delivery of microparticle danazol results in efficacy and low systemic levels.

We claim:

1. A drug formulation comprising drug particles suitable for regional administration of an effective amount to provide relief from symptoms of a disease or disorder selected from the group consisting of endometriosis, endometrial bacterial infections, cancer, and endocrine conditions in a region in patients in need thereof, wherein the region is selected from the group consisting of the uterus, fallopian tubes, peritoneal space, pelvic cul-de-sac, ovaries, and urinogenital tract, wherein the effective amount is a dosage which results in low serum drug levels and reduced side effects as compared to systemic administration of the drug, and wherein the formulation is in a carrier promoting quick uptake of the drug into the blood stream, a carrier manipulating release of drug, or a carrier promoting adhesion of the drug selected from the group consisting of a liquid suspension or dispersion, a hydrogel suspension or dispersion, a topical ointment, a cream, a lotion, and a foam.

2. The formulation of claim 1 wherein the region is the female reproductive organs.

3. The formulation of claim 2 wherein the patients have a disorder located in the reproductive organs.

4. A method of treating a patient having a disease or disorder selected from the group consisting of endometriosis, endometrial bacterial infections, cancer, and endocrine conditions comprising the step of topically administering to the patient a drug formulation suitable for regional administration comprising an effective amount of drug to provide relief from symptoms of the disease or disorder in a region in the patient in need thereof, wherein the region is selected from the group consisting of the uterus, fallopian tubes, peritoneal space, pelvic cul-de-sac, ovaries, and urinogenital tract, wherein the effective amount of drug is a dosage which results in low serum drug levels with reduced side effects as compared to system administration of the drug, and wherein the formulation is in a carrier promoting quick uptake of the drug into the blood stream, a carrier manipulating release of drug, or a carrier promoting adhesion of the drug selected from the group consisting of a liquid suspension or dispersion, a hydrogel suspension or dispersion, a topical ointment, a cream, a lotion, and a foam.

5. The formulation of claim 3 wherein the drug is for treatment of endometriosis and is selected from the group consisting progestins, estrogens, antiestrogens and antiprogestins.

6. The formulation of claim 1 wherein the drug is in the form of micro or nano particulates and wherein the particulates adhere to mucosal tissue.

7. The formulation of claim 1 wherein the drug is in the form of micro or nano particulates and wherein the particulates comprise polymer which alters the rates of drug absorption in the region to be treated.

8. The formulation of claim 1 which can be administered vaginally, intraperitoneally, or directly on the reproductive organs of interest.

9. The formulation of claim 8 wherein the drug is danazole and wherein the formulation is suitable for vaginal administration in patients in need thereof and is in a dosage effective for treatment of endometriosis.

10. The formulation of claim 1 wherein the drug is selected from the group consisting of an anticancer drug, a cytotherapeutic and an anti-proliferative drug in a dosage effective for treatment of cancer in the region of the patient where administered.

11. A method for treating endometriosis comprising administering to the mucosal membranes of the female reproductive tract particulate danazole in a carrier promoting quick uptake of the drug into the blood stream, a carrier manipulating release of drug, or a carrier promoting adhesion of the drug, wherein the carrier is selected from the group consisting of a liquid suspension or dispersion, a hydrogel suspension or dispersion, a topical ointment, a cream, a lotion, and a foam, wherein the dosage of the danazole is effective to reduce the symptoms of endometriosis without causing blood levels of danazole achieved with systemic administration of the danazole.

12. A composition for treating endometriosis comprising particulate danazole in a carrier promoting quick uptake of the drug into the blood stream, a carrier manipulating release of drug, or a carrier promoting adhesion of the drug, when applied to the mucosal membranes of the female reproductive tract, wherein the carrier is selected from the group consisting of a liquid suspension or dispersion, a hydrogel suspension or dispersion, a topical ointment, a cream, a lotion, and a foam wherein the dosage of the danazole is effective to reduce the symptoms of endometriosis without causing blood levels of danazole achieved with systemic administration of the danazole.

13. The formulation of claim 1 wherein the drug is an antibacterial agent effective for treatment of endometrial bacterial infections.

14. The formulation of claim 1 wherein the drug has steroidal activity suitable for treatment of endocrine conditions.

15. The formulation of claim 1 wherein the drug is effective for treatment of endocrine conditions selected from the group consisting of menopause, infertility, contraception, dysfunctional uterine bleeding, dysmenorrhea, adenomyosis, and assisted reproductive technologies.

16. The composition of claim 12 wherein the danazole is in an effective dosage for treating endometriosis when applied to the uterus and causes reduced side effects.

17. The method of claim 4 wherein the region is the female reproductive organs.

18. The method of claim 17 wherein the patient has a disorder located in the reproductive organs.

19. The method of claim 18 wherein the drug is for treatment of endometriosis and is selected from the group consisting progestins, estrogens, antiestrogens and antiprogestins and the patient has endometriosis.

20. The method of claim 17 wherein the step of administration is selected from the group consisting of vaginal administration, intraperiotoneal administration and direct administration.

21. The method of claim 4 wherein the drug is danazole and wherein the formulation is vaginally administered in the patient in need thereof in a dosage effective for treatment of endometriosis.

22. The method of claim 4 wherein the drug is selected from the group consisting of an anticancer drug, a cytotherapeutic and an anti-proliferative drug in a dosage effective for treatment of cancer in the region of the patient where administered.

23. The method of claim 1 wherein the drug is an antibacterial agent effective for treatment of endometrial bacterial infections.

24. The method of claim 4 wherein the drug has steroidal activity suitable for treatment of endocrine conditions.

25. The method of claim 16 wherein the drug is effective for treatment of endometrial bacterial infections selected from the group consisting of menopause, infertility, contraception, dysfunctional uterine bleeding, dysmenorrhea, adenomyosis, and assisted reproductive technologies.

26. The method of claim 11 wherein the danazole is in a form suitable for application to the uterus.

* * * * *

UNITED STATES PATENT AND TRADEMARK OFFICE
CERTIFICATE OF CORRECTION

| | |
|---|---|
| PATENT NO. | : 6,416,778 B1 |
| APPLICATION NO. | : 09/355213 |
| DATED | : July 9, 2002 |
| INVENTOR(S) | : Vanaja V. Ragavan and Gerianne M. DiPiano |

It is certified that error appears in the above-identified patent and that said Letters Patent is hereby corrected as shown below:

Title page, item (60), at "Related U.S. Application Data", insert --Continuation-in-part of application No. 08/971,346, Filed Nov. 17, 1997, now Pat. No. 5,993,856--.

Column 1, line 6, insert --application No. 08/971,346, Filed Nov, 17, 1997, now Pat. No. 5,993,856-- after "claims the benefit of" and before "Provisional Application Nos".

Signed and Sealed this
Twenty-third Day of August, 2011

David J. Kappos
*Director of the United States Patent and Trademark Office*